United States Patent [19]

Fruehwirth

[11] Patent Number: Plant 7,716

[45] Date of Patent: Nov. 19, 1991

[54] POINSETTIA PLANT 'LILO PINK'

[75] Inventor: Franz Fruehwirth, Encinitas, Calif.

[73] Assignee: Paul Ecke Ranch, Inc., Encinitas, Calif.

[21] Appl. No.: 528,236

[22] Filed: May 24, 1990

[51] Int. Cl.[5] ..... A01H 5/00

[52] U.S. Cl. ..... Plt./86

[58] Field of Search ..... Plt./86, 86.1, 86.3

*Primary Examiner*—Howard J. Locker

*Attorney, Agent, or Firm*—Arnold, White & Durkee

[57] ABSTRACT

Poinsettia 'Lilo Pink' is a new cultivar, distinguished by dark pink bracts and intense dark green foliage with self-branching characteristics. 'Lilo Pink' is a color sport of the dark red bracted 'Lilo' (U.S. Plant Pat. No. 6,694) with the same flowering response and cultural requirements. The new plant produces a very desirable branched flowering pot plant. The new plant is resistant to epinasty after being confined to shipping containers and recovers rapidly if the plant does become epinastic. The post-production foliage and bract retention is excellent even under low light intensities in the consumer's home.

1 Drawing Sheet

BACKGROUND OF THE NEW PLANT

This new poinsettia cultivar originated as a pink sport of 'Lilo' (U.S. Plant Pat. No. 6,694) in my greenhouse in Encinitas, Calif. It was selected because of its early flowering, self branching, dark pink flower bracts and dark green foliage; traits which distinguish it from other poinsettia cultivars, and seem to make it a desirable plant for commercial greenhouse production. After selection, stem cuttings of this plant were vegetatively reproduced for test purposes in Encinitas, Calif., and clones of this plant were subjected to successive generations of vegetative propagation which demonstrated that its distinctive characteristics hold true from generation to generation.

DESCRIPTION OF THE PHOTOGRAPHS

Poinsettia 'Lilo Pink' is illustrated in the accompanying color photographs.

The upper photo is a side view of a typical branched plant in full flower.

The lower photo is a top view of the same plant showing flower and bract formation.

DESCRIPTION OF THE PLANT

The following is a detailed description of this new poinsettia as observed in my greenhouse in Encinitas, Calif., during December 1989. Observations were recorded from flowering plants, grown as 3 unpinched plants per pot. The pot was 14 cm. in diameter and 11 cm. in height. Color designations are compared to the 1986 edition of R.H.S. Colour Chart, first published in 1966 by The Royal Horticultural Society, London, England.

THE PLANT

Origin: Sport of 'Lilo' (U.S. Plant Pat. No. 6,694).

Classification:

*Botanic.*—*Euphorbia pulcherrima* Willd.

*Common name.*—Poinsettia.

*Cultivar name.*—'Lilo Pink.'

Form: Shrub.

Height: Medium.

Growth habit: As a single stemmed plant, upright and vigorous with many self-branching side shoots. The application of a chemical growth retardant may be needed to restrict height for commercial pot plant production. I observed 3 plants in a pot with an overall height of 41 cm. and an overall width of 51 cm. The bract diameter of individual flowers was 32 cm.

Branching: Axillary branches will develop and terminate in a flower without pinching. However, it is usually desirable to pinch 'Lilo Pink' and remove all terminal dominance. Then, all axillary branches will develop uniformly and at a faster rate.

Growth rate: Rooting of stem cuttings occurs in 12–18 days under intermittent mist. The plant will flower in about nine weeks under continuous long night conditions and night temperatures of about 16–18 degrees C.

Foliage: The foliage is clean and uniformly dark green from bottom to top of the plant. The leaves are of medium size, leaf blades typically being about 10–14 cm. long and about 8–10 cm. wide with leaf petioles about 5–7 cm. long.

Leaf shape: Typical leaves are generally ovate with obtuse bases and acuminate tips. Leaf margins are entire or weakly lobed with 1 or 2 indentations of each side of the leaf blade.

*Color.*—*Upper side — Dark green, darker than R.H.S.* 147A. Under side — Green, between R.H.S. 137B and R.H.S. 137C.

*Retention.*—The foliage lasts extremely well even under low light intensities in the consumer's home.

Bracts: Generally there are 24–27 pink bracts of various sizes subtending the cyathia. The primary bracts have blades typically 12–15 cm. long and 8–10 cm. wide with petioles about 2-cm. long.

*Shape.*—Bracts are mostly ovate to elliptic with acute bases and acuminate tips. Primary bracts are weakly lobed with 1 or 2 indentations on either side of the bract. Secondary bracts have entire margins.

*Color.*—Upper side — Dark pink, near R.H.S. 53D. Under side — Pink, between R.H.S. 51B and R.H.S. 51C.

Flowers: Generally, 21–24 cyathia (flowers) are present when the plant is in full bloom. Each cyathium is about 7–8 mm long and about 5 mm wide, green in color, and fringed with dark pink at the distal end. A yellow nectar cup protrudes from the side of each cyathium. The flower pedicel is also green and about 7–8 mm in length. The stamens protruding from the cyathia are pinkish-white.

What is claimed:

1. A new and distinct poinsettia cultivar, substantially as herein shown and described, characterized by its early flowering, self-branching, dark pink flower bracts and dark green foliage.

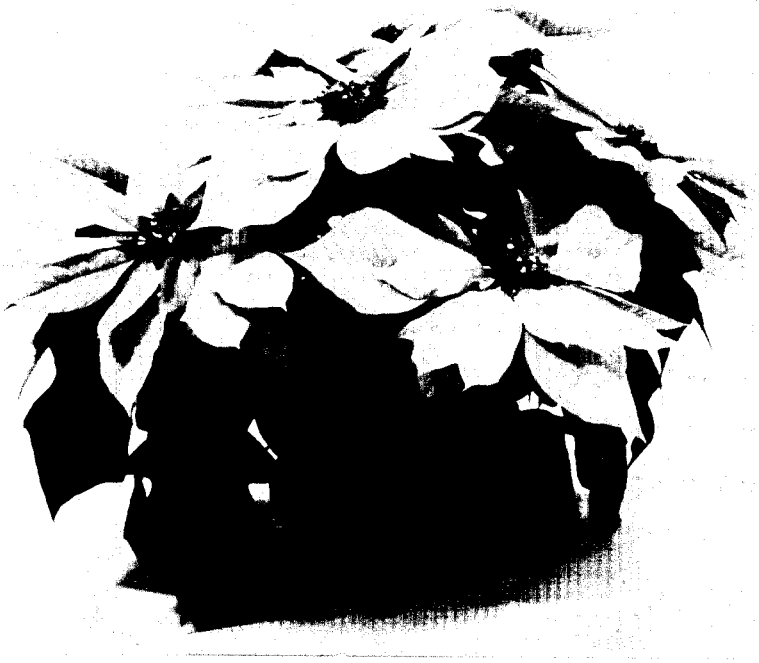
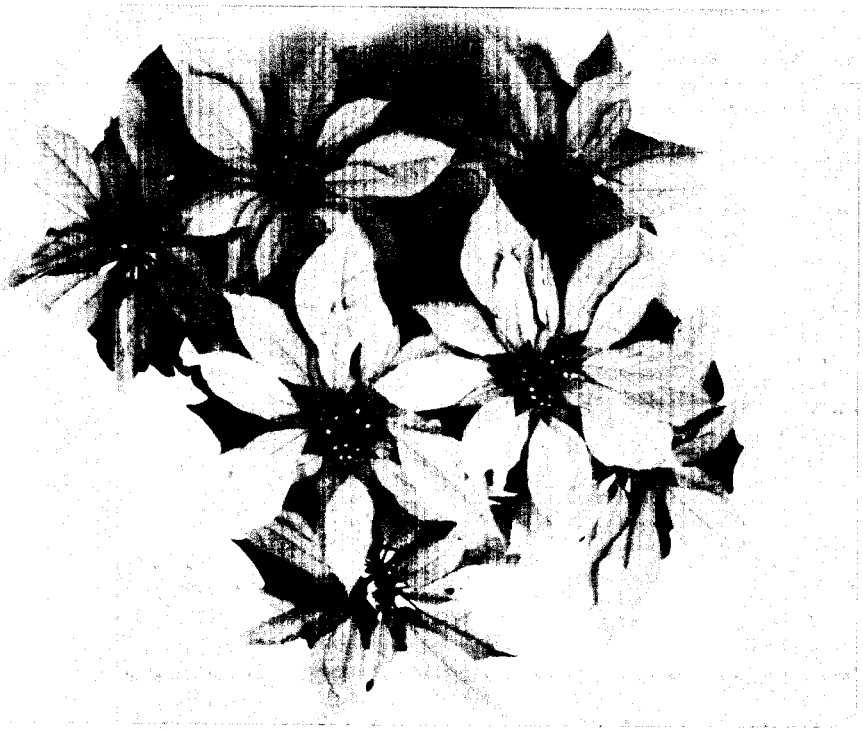

* * * * *